US010966665B2

(12) United States Patent
Lee (10) Patent No.: US 10,966,665 B2
(45) Date of Patent: Apr. 6, 2021

(54) METHOD AND APPARATUS FOR CALCULATING BIOMETRIC INDEX USING BIOMETRIC INFORMATION

(71) Applicant: ONESOFTDIGM CO., LTD, Pohang-si (KR)

(72) Inventor: Dae Ho Lee, Pohang-si (KR)

(73) Assignee: ONESOFTDIGM CO., LTD, Pohang-si (KR)

( * ) Notice: Subject to any disclaimer, the term of this patent is extended or adjusted under 35 U.S.C. 154(b) by 158 days.

(21) Appl. No.: 16/064,385

(22) PCT Filed: Nov. 11, 2016

(86) PCT No.: PCT/KR2016/012979
§ 371 (c)(1),
(2) Date: Jul. 31, 2018

(87) PCT Pub. No.: WO2017/111308
PCT Pub. Date: Jun. 29, 2017

(65) Prior Publication Data
US 2019/0000398 A1    Jan. 3, 2019

(30) Foreign Application Priority Data
Dec. 22, 2015    (KR) ........................ 10-2015-0183871

(51) Int. Cl.
*A61B 5/024* (2006.01)
*A61B 5/00* (2006.01)
(Continued)

(52) U.S. Cl.
CPC .............. *A61B 5/7225* (2013.01); *A61B 5/00* (2013.01); *A61B 5/0205* (2013.01); *A61B 5/117* (2013.01);
(Continued)

(58) Field of Classification Search
CPC ........ G16H 20/30; G16H 50/30; G16H 50/20; G16H 20/60; G16H 20/70; A61B 5/0205; A61B 5/117
See application file for complete search history.

(56) References Cited

U.S. PATENT DOCUMENTS

| 2011/0087137 A1* | 4/2011 | Hanoun | G06F 19/3418 600/587 |
| 2013/0131465 A1* | 5/2013 | Yamamoto | A61B 5/7271 600/301 |
| 2015/0164351 A1* | 6/2015 | He | H05B 47/105 702/19 |

FOREIGN PATENT DOCUMENTS

| KR | 20040043981 A | * | 5/2004 | |
| KR | 20090000117 A | * | 1/2009 | ............. G16H 50/30 |

(Continued)

*Primary Examiner* — Allen Porter
*Assistant Examiner* — Adreanne A. Arnold
(74) *Attorney, Agent, or Firm* — Goldilocks Zone IP Law (57) ABSTRACT

A method and an apparatus for calculating a biometric index using biometric information are disclosed. An apparatus for calculating a biometric index using biometric information is provided, the apparatus comprising: a transmission/reception unit for receiving biometric information collected by a user terminal or a biometric information collection apparatus; a storage unit for storing an index calculation formula for calculating a biometric index and a daily body index using the biometric information and daily body index; an extraction unit for extracting the stored biometric information and index calculation formula; and a calculation unit for calculating a biometric index and a daily body index using the received biometric information and the predetermined index calculation formula, wherein the biometric index includes one or more of an eating behavior index, an activity index, a sleep index and a heart rate variability index, and calculates the daily body index using the biometric index.

8 Claims, 3 Drawing Sheets

(51) Int. Cl.
*G16H 20/70* (2018.01)
*A61B 5/117* (2016.01)
*G16H 50/30* (2018.01)
*G16H 20/60* (2018.01)
*G16H 20/30* (2018.01)
*G16H 50/20* (2018.01)
*A61B 5/0205* (2006.01)
*A61B 5/11* (2006.01)

(52) U.S. Cl.
CPC ............. *G16H 20/30* (2018.01); *G16H 20/60* (2018.01); *G16H 20/70* (2018.01); *G16H 50/20* (2018.01); *G16H 50/30* (2018.01); *A61B 5/02405* (2013.01); *A61B 5/1118* (2013.01); *A61B 5/4815* (2013.01); *A61B 5/4866* (2013.01)

(56) References Cited

FOREIGN PATENT DOCUMENTS

| KR | 10-2012-0057281 A | 6/2012 |
| KR | 10-2013-0040494 A | 4/2013 |
| KR | 10-2015-0101179 A | 9/2015 |

\* cited by examiner

METHOD AND APPARATUS FOR CALCULATING BIOMETRIC INDEX USING BIOMETRIC INFORMATION

CROSS-REFERENCE TO RELATED APPLICATIONS

This application claims priority to and the benefit under 35 U.S.C. Section 371, of PCT International Application No. PCT/KR2016/012979, filed Nov. 11, 2016, which claimed priority to Korean Patent Application No. 10-2015-0183871, filed on Dec. 22, 2015, the disclosure of which is incorporated herein by reference in its entirety.

TECHNICAL FIELD

The present invention relates to a technology for calculating a biometric index by measuring and inputting biometric information, and more particularly, to a technology for receiving measured biometric information from a user terminal and a biometric information collecting device and calculating a biometric index.

BACKGROUND ART

With the steadily increasing interest in health issues, many people want to know their body conditions these days.

In most past cases, experts interpreted biometric index measurement results, such as blood pressure, blood flow, and glucose measured by measurement devices, so that diagnoses might be made. Recently, telemedicine services are being provided by transmitting and receiving such measurement results by utilizing communication technology. However, it is difficult for the public who are not experts to understand such measurement results and guess their body conditions.

Also, questionnaires used for existing medical consultation are not uniformized, and interpretation thereof is evaluated in contradictory ways in some cases.

Therefore, uniform indices should be used so that health conditions can be evaluated from the viewpoint of the public.

Korean Patent No. 10-1503836 discloses an apparatus and method for calculating a physical age. The apparatus for calculating a physical age according to Korean Patent No. 10-1503836 includes a calculation unit which calculates a physical age of a user by using at least one of the user's back strength, measured high jump value, number of sit-ups, grasping power, height, measured sitting trunk flexion value, maximum oxygen intake, reaction time, weight, and eye-closed single-leg stance duration, and an output unit which outputs the calculated physical age of the user.

Korean Patent No. 10-1503836 is characterized by calculating a physical age but lacks indices for evaluating overall health conditions not only in a physical aspect but also in various aspects.

DISCLOSURE

Technical Problem

The purpose of the present invention is to provide a method for calculating a biometric index by using biometric information.

Another purpose of the present invention is to provide an apparatus for calculating a biometric index by using biometric information.

Technical Solution

In an aspect of the present invention to achieve the above-described objective, an apparatus for calculating a biometric index by using biometric information may comprise a transmission and reception unit configured to receive biometric information collected by a user terminal or a biometric information collecting device, a storage unit configured to store index calculation formulae for calculating biometric indices and a daily physical index by using the biometric information, the received biometric information, calculated biometric indices, and a calculated daily physical index, an extraction unit configured to extract the stored biometric information and index calculation formulae and a calculation unit configured to calculate the biometric indices and the daily physical index by using the received biometric information and the preset index calculation formulae, wherein the biometric indices include at least one of a diet action index, an activity index, a sleeping index, and a heart rate variability (HRV) index, and the biometric indices are used to calculate the daily physical index.

Here, the diet action index may be a value calculated according to an equation below:

$$\text{Diet Action Index} = \max\left(0, \left[\frac{\text{Number of meals per day}}{3} - \frac{\text{Overdrunk or not}}{3}\right]\right) \times 100$$

(a case of overdrinking corresponds to 1, a case of none overdrinking corresponds to 0, and the number of meals per day is an integer greater than or equal to 0 and less than or equal to 3).

Here, the activity index may be a value calculated according to an equation below:

$$\text{Activity Index} = \min\left(1, \frac{\text{Actual Calorie Consumption}}{\text{Required Energy per Day}}\right) \times 100.$$

Here, the sleeping index may be a value calculated according to an equation below:

$$\text{Sleeping Index} = \\ \max\left\{0, \left(\frac{1}{2} \times \text{Sleep Efficiency} + \frac{1}{2} \times \text{Satisfied Golden Time Rate} - \right.\right.\\ \left.\left.\text{Sleeping Hour Penalty}\right)\right\}$$

$$\left(\text{Here, Sleep Efficiency} = \frac{\text{Actual Sleeping Hours}}{\text{All Sleeping Hours}} \times 100,\right.$$

$$\text{Satisfied Golden Time Rate} = \frac{\text{Golden Time Sleeping Hours}}{4 \text{ Hours}} \times 100, \text{ and}$$

$$\text{Sleeping Hour Penalty} = \\ \left. 5 \times \max\{0, (\text{Recommended Sleeping Hours per Day} - \right.\\ \left.\text{Actual Sleeping Hours})\}\right).$$

Here, the HRV index may be a value calculated according to an equation below:

$$\text{HRV Index} = 100 \times (\tfrac{2}{3} \cdot \text{LF Score} + \tfrac{1}{3} \cdot \text{HF Score})$$

(Here, when a low-frequency region is set to 0.04 Hz to 0.15 Hz and a high-frequency region is set to 0.18 Hz to 0.4 Hz, it is determined that $$LF\ Score = \begin{cases} \dfrac{LF}{6.00} & (0 \le LF \le 6.00) \\ 1 & (6.00 \le LF \le 8.06) \\ 1 - 0.5\dfrac{LF - 8.06}{12 - 8.06} & (8.06 \le LF \le 12) \end{cases},$$

$$HF\ Score = \begin{cases} \dfrac{HF}{4.00} & (0 \le HF \le 4.00) \\ 1 & (4.00 \le HF \le 7.23) \\ 1 - 0.5\dfrac{HF - 7.23}{12 - 7.23} & (7.23 \le HF \le 12), \end{cases} \quad LF = \ln\left(\int_{0.04}^{0.15} PSD\ df\right)$$

and $$HF = \ln\left(\int_{0.18}^{0.4} PSDdf\right).$$

Here, the daily physical index may be a value calculated according to an equation below:

Daily Physical Index=a×Diet Action Index+b×Sleeping Action Index+c×Activity Index+d×HRV Index (Here, a+b+c+d=1, each of a, b, c, and d is determined to be an arbitrary value greater than 0 and less than 1, and when identical weights are given to all the indices as an example, it is determined that a=b=c=d=¼).

Here, the calculation unit additionally may calculate a time-series diagram, an average, and a standard deviation of at least one of the biometric indices and the daily physical index.

Here, the storage unit may store at least one of the calculated biometric indices and daily physical index for each preset time period.

In another aspect of the present invention to achieve the above-described objective, a method for a biometric index calculation apparatus to calculate a biometric index by using biometric information may comprise receiving biometric information transmitted by a user terminal or a biometric information collecting device, storing the received biometric information in association with identification information of the user terminal or the biometric information collecting device, extracting the stored biometric information and calculating biometric indices and a daily physical index by using the extracted biometric information according to preset index calculation formulae, wherein the biometric indices include at least one of a diet action index, an activity index, a sleeping index, and a heart rate variability (HRV) index, and the biometric indices are used to calculate the daily physical index.

Here, the method may further comprise, after the calculating of the biometric indices and the daily physical index, transmitting the calculated biometric indices and daily physical index to the user terminal via a wired or wireless network.

Here, the calculating of the biometric indices and the daily physical index may comprise additionally calculating a time-series diagram, an average, and a standard deviation of at least one of the biometric indices and the daily physical index.

Advantageous Effects

According to the apparatus and method for calculating a biometric index by using biometric information, data is generated from daily activities, such as sleeping, dining, stress, and walking, and biometric indices and a daily physical index are calculated, so that physical or health conditions can be evaluated in various aspects.

Also, the public can easily understand their physical or health conditions. Further, various calculated index information is stored as a database and used to run a counseling center, develop a product, and provide a service in a service industry, thereby helping in industrial development in the end.

MODES OF THE INVENTION

The present invention may be variously modified and may include various embodiments. However, particular embodiments are exemplarily illustrated in the drawings and will be described in detail. However, it should be understood that the particular embodiments are not intended to limit the present disclosure to specific forms, but rather the present disclosure is meant to cover all modification, similarities, and alternatives which are included in the spirit and scope of the present disclosure. Like reference numerals refer to like elements throughout the description of the drawings.

Relational terms such as first, second, A, B, and the like may be used for describing various elements, but the elements should not be limited by the terms. The terms are used solely for distinguishing one element from another. For instance, without departing the scope of the present disclosure, a first element may be named as a second element, and similarly, a second element may be named as a first element. The term "and/or" encompasses both combinations of the plurality of related items disclosed and any item from among the plurality of related items disclosed.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The terminology used herein is not for delimiting the present invention but for describing the specific embodiments. The terms of a singular form may include plural forms unless otherwise specified. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, exemplary embodiments of the present invention will be described in detail with reference to the accompanying drawings.

Figure 1:
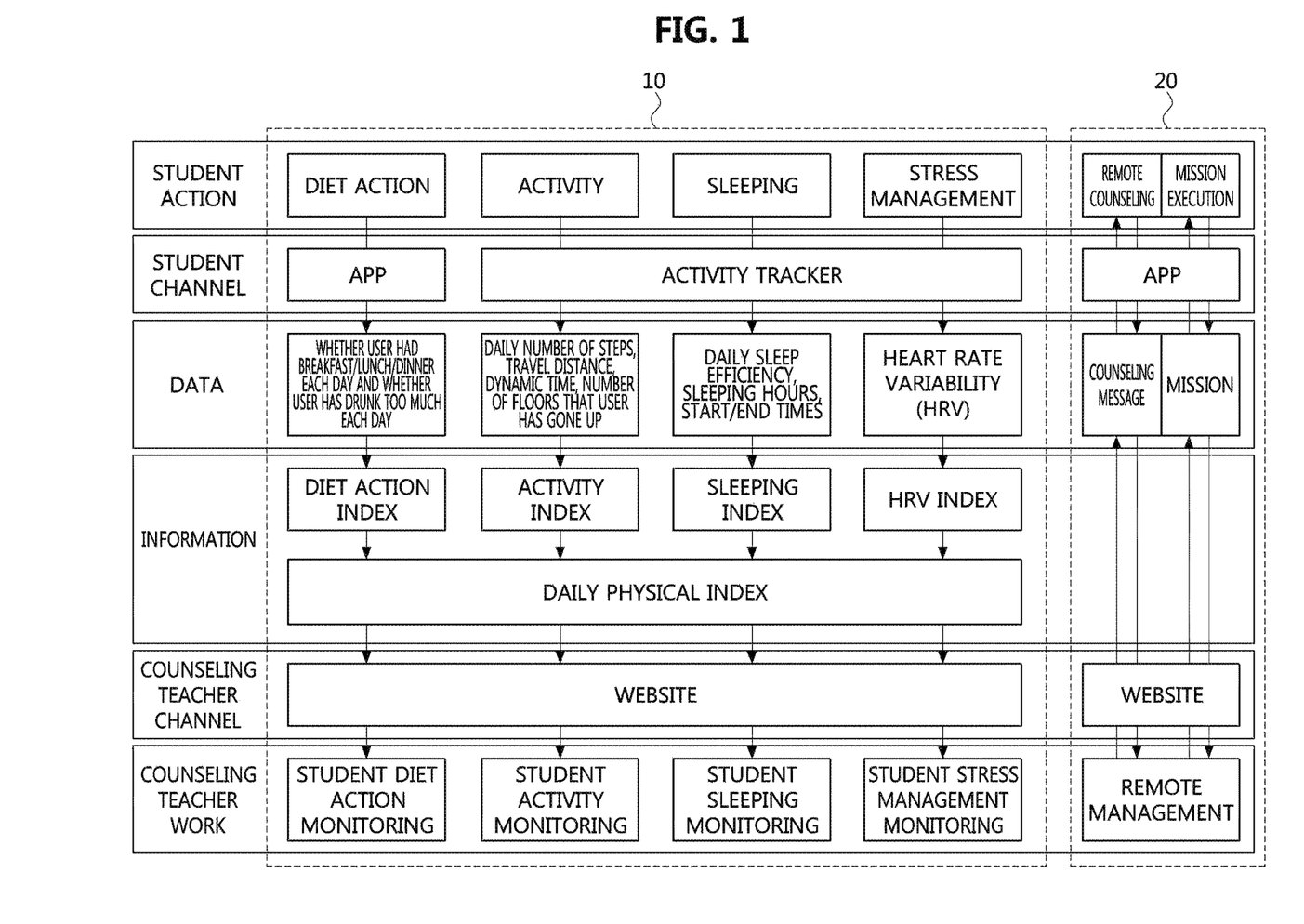
FIG. 1 is a conceptual diagram illustrating an environment in which an apparatus and method for calculating a biometric index by using biometric information according to an embodiment of the present invention are used.

FIG. 1 is a conceptual diagram illustrating an environment in which an apparatus and method for calculating a biometric index by using biometric information according to an embodiment of the present invention are used.

An environment in which an apparatus and method for calculating a biometric index by using biometric information are used will be described with reference to FIG. 1. As an example, a remote counseling system for students will be described, but the present invention is not intended for only students or not limited to a consultation system.

A method of calculating a biometric index by using biometric information with respect to students may be described with a hierarchical concept which is classified as follows.

The hierarchy may be subdivided into, for example, student action, student channel, data, information, counseling-teacher channel, and counseling-teacher work.

Also, the hierarchy may be subdivided into a monitoring and biometric information collecting part 10 and a remote counseling part 20 according to roles. Each part will be described below, centering on layers.

First, in the monitoring and biometric information collecting part 10, a student action layer may denote actual behavior of students, such as diet actions, sleeping, activities, and stress.

A student channel layer is an information collection passage and may denote user terminals (an application (App)) or biometric information collecting devices (activity trackers) which are used or worn by students.

A data layer is information representing behavior and may be embodied as the number of meals, the number of steps, sleeping hours, heart rate variability (HRV), and the like.

An information layer is information generated on the basis of information of the data layer and may be represented as biometric indices and a daily physical index. For example, the biometric indices may be represented as a diet action index, an activity index, a sleeping index, and an HRV index, and the daily physical index may be calculated on the basis of the biometric indices.

A counseling-teacher channel layer is intended to provide an interface for remote counseling and may denote a remote counseling device or a website accessed by a remote counseling device. Here, the remote counseling device may be a computer or a mobile terminal used by a counseling teacher.

A counseling-teacher work layer may denote activities of a counseling teacher monitoring activities of respective students through the counseling-teacher channel layer.

The user terminal, the biometric information collecting device, the biometric indices, and the daily physical index will be described below.

Next, referring to the remote counseling part 20, the student action layer may denote activities for requesting counseling and executing a mission, and the student channel layer may denote a user terminal (an App) as a passage for remote counseling.

The data layer is information exchanged for remote counseling and may denote counseling (request and response) messages and details of missions given by a counseling teacher.

The counseling-teacher channel layer may denote a remote counseling device through which it is possible to exchange counseling messages and the mission details with user terminals of students without any additional processing.

The counseling-teacher work layer may denote an activity of a counseling teacher remotely counseling students on the basis of collected or monitored information. For example, the collected or monitored information may denote biometric indices and a daily physical index calculated by the monitoring and biometric information collecting part 10.

For example, when a specific student has a daily physical index of 50 points and other students whose ages are the same as or similar to an age of the specific student have an average daily physical index of 70 points, 70 points may be given as a target (a mission), and items of biometric indices which are particularly required to achieve the target may be suggested as the mission details.

The counseling messages include counseling requests, questions, and answers and include several messages exchanged between a counselor and students on the basis of various biometric indices and daily physical indices.

Figure 2:
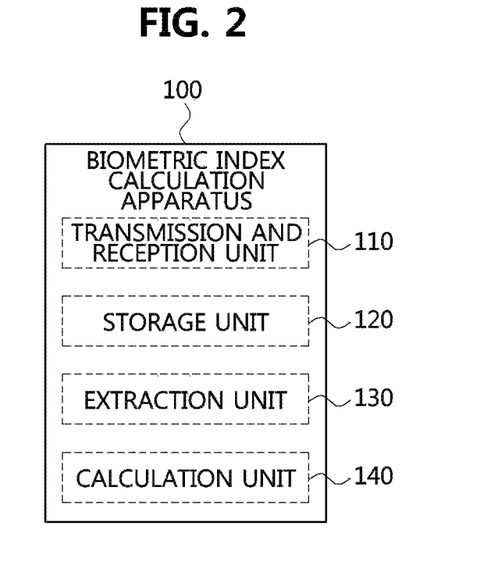
FIG. 2 is a block diagram of an apparatus for calculating a biometric index by using biometric information according to an embodiment of the present invention.

FIG. 2 is a block diagram of an apparatus for calculating a biometric index by using biometric information according to an embodiment of the present invention.

Referring to FIG. 2, a biometric index calculation apparatus 100 may include a transmission and reception unit 110, a storage unit 120, an extraction unit 130, and a calculation unit 140.

The transmission and reception unit 110 is connected to a wired or wireless network and receives biometric information transmitted from a user terminal or a biometric information collecting device. For example, the biometric information may include the number of meals per day, whether a user has drunk too much, the number of steps, a travel distance, a travel time, the number of floors that the user has gone up, sleeping hours per day, a start time and an end time of sleeping, actual sleeping hours, and an HRV test result.

Here, the HRV test result denotes a frequency-dependent power spectral density result. Also, the transmission and reception unit 110 may transmit biometric indices and a daily physical index calculated according to preset index calculation formulae to the user terminal via a wired or wireless network in response to a request of the user terminal. The wired or wireless network may be variously determined to be the Internet, a fiber-optic local area network (LAN), a Long Term Evolution (LTE) network, and the like.

The biometric information collecting device may be various measurement devices including a pedometer for measuring the number of steps and a travel distance per day, a device for measuring an HRV, and the like.

The user terminal may be any types of devices, such as a cellular phone, a personal digital assistant (PDA), a laptop computer, and a desktop computer, which are capable of short-range communication and long-range communication via a wired or wireless network and to which data can be input by a user.

The storage unit 120 stores formulae for calculating biometric indices and a daily physical index by using the biometric information. Also, the storage unit 120 may store the received biometric information in association with user terminal identification information, and store calculated biometric indices and daily physical index. Here, the user terminal identification information may be variously selected by a user or a manufacturer of the biometric index calculation apparatus. For example, the user terminal may be identified with an identification (ID), a password, an address, an age, and the like.

In addition, the storage unit 120 may store at least one of the calculated biometric indices and daily physical index for each preset period. Here, the preset period may be every week, every month, or every year.

The extraction unit 130 extracts biometric information from the storage unit 120 to calculate the biometric indices and the daily physical index. Here, the extraction unit 130 also extracts preset biometric index and daily physical index calculation formulae so that the calculation unit 140 may calculate the biometric indices and the daily physical index.

The calculation unit 140 calculates the biometric indices and the daily physical index by using the extracted biometric information and index calculation formulae. Here, the biometric indices may include at least one of a diet action index, an activity index, a sleeping index, and an HRV index.

Each of the preset index calculation formulae will be described in detail below.

First, the diet action index may be determined by a relationship between the number of meals per day and whether a user has drunk too much and is in accordance with, for example, the following equation.

$$\text{Diet Action Index} = \max\left(0, \left[\frac{\text{Number of meals per day}}{3} - \frac{\text{Overdrunk or not}}{3}\right]\right) \times 100 \quad \text{[Equation 1]}$$

(the case of overdrinking corresponds to 1, the case of none overdrinking corresponds to 0, and the number of meals per day is an integer greater than or equal to 0 and less than or equal to 3)

The activity index may be determined by using a relationship between a calorie consumption and recommended daily calories according to, for example, the following equation.

$$\text{Activity Index} = \min\left(1, \frac{\text{Actual Calorie Consumption}}{\text{Required Energy per Day}}\right) \times 100 \quad \text{[Equation 2]}$$

The sleeping index may be determined by using a relationship among a sleep efficiency, a satisfied golden time rate, and a sleeping hour penalty according to, for example, the following equation.

$$\text{Sleeping Index} = \quad \text{[Equation 3]}$$
$$\max\left\{0, \left(\frac{1}{2} \times \text{Sleep Efficiency} + \frac{1}{2} \times \text{Satisfied Golden}\right.\right.$$

$$\left.\left.\text{Time Rate} - \text{Sleeping Hour Penalty}\right)\right\}$$

$$\left(\text{Here, Sleep Efficiency} = \frac{\text{Actual Sleeping Hours}}{\text{All Sleeping Hours}} \times 100,\right.$$

Satisfied Golden Time Rate =

$$\frac{\text{Golden Time Sleeping Hours}}{4 \text{ Hours}} \times 100, \text{ and}$$

Sleeping Hour Penalty =

$$5 \times \max\{0, (\text{Recommended Sleeping Hours per Day} -$$

$$\left.\text{Actual Sleeping Hours})\}\right)$$

The HRV index may be determined by using a low-frequency region score (LF score) and a high-frequency region score (HF score) of a power spectral density (PSD) according to, for example, the following equation.

HRV Index=100×(⅔·LF Score+⅓·HF Score) [Equation 4]

(Here, when the low-frequency region is set to 0.04 Hz to 0.15 Hz and the high-frequency region is set to 0.18 Hz to 0.4 Hz, $$LF \text{ Score} = \begin{cases} \frac{LF}{6.00}(0 \leq LF \leq 6.00) \\ 1(6.00 \leq LF \leq 8.06) \\ 1 - 0.5\frac{LF - 8.06}{12 - 8.06}(8.06 \leq LF \leq 12) \end{cases},$$

$$HF \text{ Score} =$$

$$\begin{cases} \frac{HF}{4.00}(0 \leq HF \leq 4.00) \\ 1(4.00 \leq HF \leq 7.23) \\ 1 - 0.5\frac{HF - 7.23}{12 - 7.23}(7.23 \leq HF \leq 12) \end{cases}, \quad LF = \ln\left(\int_{0.04}^{0.15} PSDdf\right)$$

and $$HF = \ln\left(\int_{0.18}^{0.4} PSDdf\right) \text{may be determined.}$$

The daily physical index may be determined by using a relationship among the determined diet action index, sleeping index, activity index, and HRV index according to, for example, the following equation.

Daily Physical Index=a×Diet Action Index+b×Sleeping Action Index+c×Activity Index+d×HRV Index [Equation 5]

(Here, a+b+c+d=1, each of a, b, c, and d may be determined to be an arbitrary value greater than 0 and less than 1, and when the same weight is given to all the indices as an example, it is possible to determine that a=b=c=d=¼.)

In addition, variables, such as recommended sleeping hours per day, a golden time, recommended daily calories, and an actual calorie consumption, rather than constants required for the above-described index calculation formulae are previously set by the user or the manufacturer of the biometric index calculation apparatus on the basis of statistical data which may be easily obtained.

For example, daily recommended calories may be set to adult male height (m)×22×35 kcal for men and to adult female height (m)×21×35 kcal for women, the golden time may be set to a time period from 22 o'clock to 24 o'clock, and the recommended sleeping hours per day may be set to 7 hours. In particular, an actual calorie consumption may be set to 68 kcal per 30 minutes for walking, 191 kcal for jogging, 109 kcal for cycling, and the like.

The calculation unit 140 may additionally calculate a time-series diagram, an average, and a standard deviation of at least one of the biometric indices and the daily physical index. Here, the time-series diagram is a daily change graph of each index, and the average and the standard deviation are calculated on the basis of an arbitrary time period, for example, one week or one month, set by the user or the manufacturer of the biometric index calculation apparatus.

The biometric index calculation apparatus 100 may be a portable device which additionally includes a battery unit, a display unit, and a central processing unit (CPU). For example, the biometric index calculation apparatus 100 may be a smart phone or a PDA having such modules.

Figure 3:
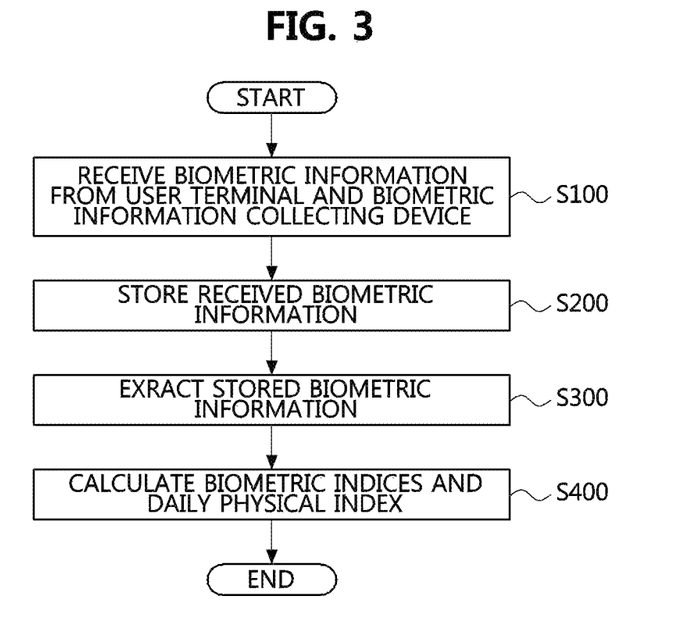
FIG. 3 is a flowchart illustrating a method of calculating a biometric index by using biometric information according to an embodiment of the present invention.

FIG. 3 is a flowchart illustrating a method of calculating a biometric index by using biometric information according to an embodiment of the present invention.

The method of calculating a biometric index by using biometric information may be performed by the above-described biometric index calculation apparatus 100.

Referring to FIG. 3, biometric information is transmitted from a user terminal or a biometric information collecting device to the biometric index calculation apparatus 100 (S100). For example, the biometric information may include the number of meals per day, whether a user has drunk too much, the number of steps, a travel distance, a travel time, the number of floors that the user has gone up, sleeping hours per day, a start time and an end time of sleeping, actual sleeping hours, and an HRV test result.

The biometric index calculation apparatus 100 stores the received biometric information in association with identification information of the user terminal or the biometric information collecting device (S200).

The biometric index calculation apparatus 100 extracts the stored biometric information (S300).

The biometric index calculation apparatus 100 calculates biometric indices and a daily physical index according to preset index calculation formulae by using the extracted biometric information (S400). Here, the biometric indices include at least one of a diet action index, an activity index, a sleeping index, and an HRV index, and formulae for calculating various biometric indices and the daily physical index may correspond to Equations 1 to 5 described above.

The biometric index calculation apparatus 100 may transmit the calculated biometric indices and daily physical index to the user terminal via a wired or wireless network.

In addition, the biometric index calculation apparatus 100 may further calculate a time-series diagram, an average, and a standard deviation of at least one of the biometric indices and the daily physical index. Here, the time-series diagram is a daily change graph of each index, and the average and the standard deviation are calculated on the basis of an arbitrary time period, for example, one week or one month set by the user or the manufacturer of the biometric index calculation apparatus.

Figure 4:
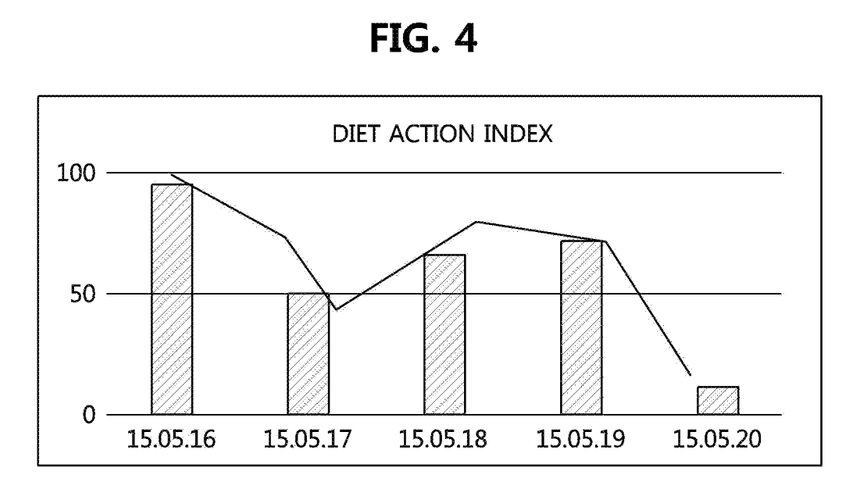
FIG. 4 is a time-series graph of a diet action index among biometric indices and a daily physical index calculated by an apparatus and method for calculating a biometric index according to an embodiment of the present invention.
Figure 5:
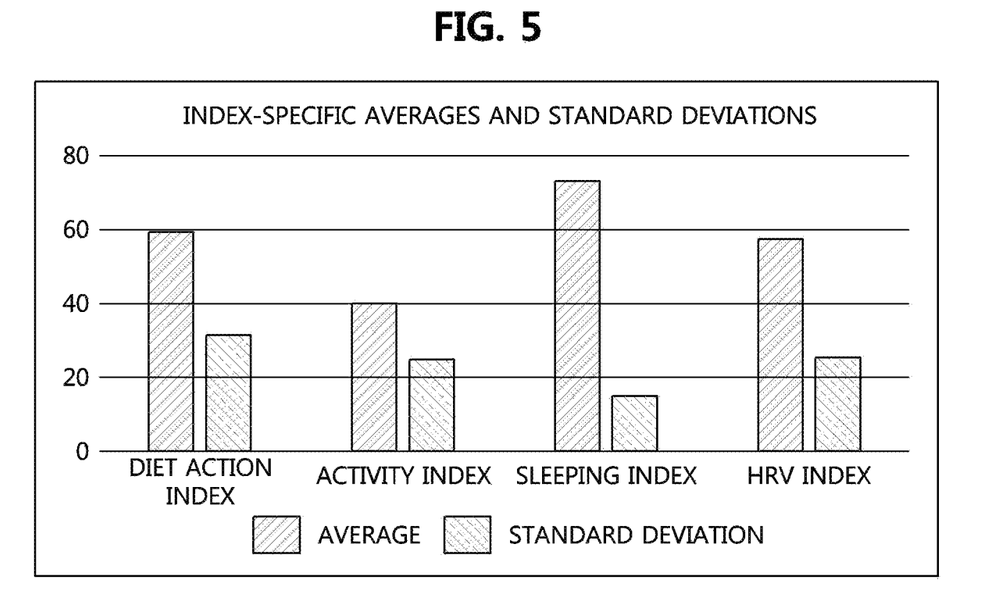
FIG. 5 is a graph of averages and standard deviations of respective biometric indices according to an embodiment of the present invention.

FIG. 4 is a time-series graph of a diet action index among biometric indices and a daily physical index calculated by an apparatus and method for calculating a biometric index according to an embodiment of the present invention, and FIG. 5 is a graph of averages and standard deviations of respective biometric indices according to an embodiment of the present invention. These graphs may be displayed in a biometric index calculation apparatus or a user terminal which receives the graphs from the biometric index calculation apparatus.

First, referring to FIG. 4, calculated daily diet action indices may be shown in the drawing on the basis of a perfect score of 100 points. A user of the user terminal or the biometric index calculation apparatus may look at the diet action indices and determine when the diet action was poor and whether the diet actions were regular.

Next, referring to FIG. 5, an average and a standard deviation of each of calculated biometric indices may be shown with the biometric indices. Here, the average and the standard deviation are calculated and displayed on the basis of a time period, for example, one week or one month, preset according to a selection of a user or a manufacturer of the biometric index calculation apparatus.

According to the above-described apparatus and method for calculating a biometric index by using biometric information, data is generated from daily activities, such as sleeping, dining, stress, and walking, and biometric indices and a daily physical index are calculated, so that physical or health conditions can be evaluated in various aspects.

Also, the public can easily understand their physical or health conditions. Further, various calculated index information is stored as a database and used to run a counseling center, develop a product, and provide a service in a service industry, thereby helping in industrial development in the end.

Although the present invention has been described above with reference to exemplary embodiments, those of ordinary skill in the art should appreciate that the present invention can be modified and altered without departing from the spirit or scope of the present invention as stated in the following claims.

The invention claimed is:

1. An apparatus for calculating a biometric index by using biometric information, the apparatus comprising:
    a processor; and
    a memory in which at least one command to be executed by the processor is stored,
    wherein the at least one command is executed to: receive biometric information collected by a user terminal or a biometric information collecting device;
        store index calculation formulae for calculating biometric indices and a daily physical index by using the biometric information, the received biometric information, calculated biometric indices, and a calculated daily physical index;
        extract the stored biometric information and index calculation formulae;
        calculate the biometric indices and the daily physical index by using the received biometric information and the preset index calculation formulae;
        transmit the calculated biometric indices and the daily physical index to the user terminal via a wired or wireless network; and
        provide user interface for the user terminal for counseling through the user terminal based on the transmitted biometric indices and the daily physical index,
    wherein the biometric indices include a heart rate variability (HRV) index and at least one of a diet action index, an activity index, and a sleeping index and the biometric indices are used to calculate the daily physical index,
    wherein the HRV index is calculated based on scoring a frequency region divided into a low frequency region and a high frequency region, wherein the HRV index is a value calculated according to an equation below;

HRV Index=100×(⅔LF Score+⅓HF Score)

wherein the $$LF\ Score = \begin{cases} \frac{LF}{6.00}(0 \le LF \le 6.00) \\ 1(6.00 \le LF \le 8.06) \\ 1-0.5\frac{LF-8.06}{12-8.06}(8.06 \le LF \le 12) \end{cases},$$

$$HF\ Score = \begin{cases} \frac{HF}{4.00}(0 \le HF \le 4.00) \\ 1(4.00 \le HF \le 7.23) \\ 1-0.5\frac{HF-7.23}{12-7.23}(7.23 \le HF \le 12) \end{cases},$$

wherein $LF=\ln(\int_{0.04}^{0.15} PSD\ df)$ $HF=\ln(\int_{0.18}^{0.4} PSD\ df)$, and wherein the PSD denotes a Power spectral density.

2. The apparatus of claim 1, wherein the diet action index is a value calculated based on information of a number of meals per day,
wherein information of the number of meals per day is received by the user terminal or the biometric information collecting device.

3. The apparatus of claim 1, wherein the activity index is a value calculated based on information of a required energy per day,
wherein information of the required energy per day is predetermined by the user terminal or the biometric information collecting device.

4. The apparatus of claim 1, wherein the daily physical index is a value calculated based on information of the "diet action index", the "sleeping action index", the "activity index" and the "HRV index".

5. The apparatus of claim 1, wherein the calculation unit additionally calculates a time-series diagram, an average, and a standard deviation of at least one of the biometric indices and the daily physical index.

6. The apparatus of claim 1, wherein the storage unit stores at least one of the calculated biometric indices and daily physical index for each preset time period.

7. A method for a biometric index calculation apparatus to calculate a biometric index by using biometric information, the method comprising:
receiving biometric information transmitted by a user terminal or a biometric information collecting device;
storing the received biometric information in association with identification information of the user terminal or the biometric information collecting device;
extracting the stored biometric information;
calculating biometric indices and a daily physical index by using the extracted biometric information according to preset index calculation formulae; and
transmitting the calculated biometric indices and the daily physical index to the user terminal via a wired or wireless network; and
providing user interface for the user terminal for counseling through the user terminal based on the transmitted biometric indices and the daily physical index,
wherein the biometric indices include a heart rate variability (HRV) index and at least one of a diet action index, an activity index, and a sleeping index and
wherein the heart rate variability (HRV) index is calculated based on scoring a frequency region divided into a low frequency region and a high frequency region,
wherein the HRV index is a value calculated according to an equation below:

HRV Index 100×(⅔LF Score+⅓HF Score)

wherein the $$LF\ Score = \begin{cases} \frac{LF}{6.00}(0 \le LF \le 6.00) \\ 1(6.00 \le LF \le 8.06) \\ 1-0.5\frac{LF-8.06}{12-8.06}(8.06 \le LF \le 12) \end{cases},$$

$$HF\ Score = \begin{cases} \frac{HF}{4.00}(0 \le HF \le 4.00) \\ 1(4.00 \le HF \le 7.23) \\ 1-0.5\frac{HF-7.23}{12-7.23}(7.23 \le HF \le 12) \end{cases},$$

wherein $LF=\ln(\int_{0.04}^{0.15} PSD\ df)$ $HF=\ln(\int_{0.18}^{0.4} PSD\ df)$, and wherein the PSD denotes a Power spectral density.

8. The method of claim 7, wherein the calculating of the biometric indices and the daily physical index comprises additionally calculating a time-series diagram, an average, and a standard deviation of at least one of the biometric indices and the daily physical index.

* * * * *